United States Patent [19]
Wiklund et al.

[11] Patent Number: 5,871,515
[45] Date of Patent: Feb. 16, 1999

[54] ATTACHMENT APPARATUS AND METHOD FOR AN IMPLANTABLE MEDICAL DEVICE EMPLOYING ULTRASONIC ENERGY

[75] Inventors: Craig L. Wiklund, Bloomington; Daniel C. Haeg, Champlin; James F. Kelley, Coon Rapids, all of Minn.

[73] Assignee: Medtronic, Inc., Minneapolis, Minn.

[21] Appl. No.: 140,973

[22] Filed: Aug. 27, 1998

Related U.S. Application Data

[62] Division of Ser. No. 904,601, Aug. 1, 1997.

[51] Int. Cl.$^6$ .................................................... A61N 1/375
[52] U.S. Cl. ................................................ 607/36; 29/515
[58] Field of Search .................................. 29/515, 592.1; 607/36–38

[56] References Cited

U.S. PATENT DOCUMENTS

| | | |
|---|---|---|
| 3,842,842 | 10/1974 | Kenney et al. ........................... 607/36 |
| 4,041,956 | 8/1977 | Purdy et al. . |
| 4,142,532 | 3/1979 | Ware ................................... 128/419 P |
| 4,182,345 | 1/1980 | Grose . |
| 4,243,042 | 1/1981 | Ware . |
| 4,248,237 | 2/1981 | Kenney . |
| 4,314,562 | 2/1982 | Ware . |
| 5,070,605 | 12/1991 | Daglow et al. . |
| 5,086,773 | 2/1992 | Ware . |
| 5,207,218 | 5/1993 | Carpentier et al. . |
| 5,431,695 | 7/1995 | Wiklund et al. . |
| 5,456,698 | 10/1995 | Byland et al. . |
| 5,522,861 | 6/1996 | Sikorski et al. . |
| 5,535,097 | 7/1996 | Ruben et al. . |
| 5,755,743 | 5/1998 | Volz et al. ................................ 607/37 |

OTHER PUBLICATIONS

"Ultrasonic Molding of Plastic Powders" Satinder Nayer, Avraham Benatar, The Ohio State University, Design and Manufacutring of Advanced Composites, Dearborn, Michigan USA Sep. 25–28, 1989.

"Three New Ways to Fabricate Plastics—Ultrasonically", Corporate Sourece: Branson Sonic Power Co., Sourece: Plast.Technol.; 24 No.9, Aug. 1978, pp. 37–39; Journal Announcement: 7812 Rapra Update: 8201.

"Ultrasonic Pressing of Plastic–Film Capacitor", Kaneko, Seiji, Zhu, Weihong, Gakumazawa, Masahide, Sinoda, Kiyoshi, Corporate Sourece: Shibaura Inst. of Technology, Tokyo, Japan; Converence Title: Proceedings of the Ultrasonics International Conference; Conference Location: Vienna, Austria.

(List continued on next page.)

*Primary Examiner*—William E. Kamm
*Assistant Examiner*—George R. Evanisko
*Attorney, Agent, or Firm*—Thomas F. Woods; Harold R. Patton

[57] ABSTRACT

A method and apparatus for attaching a pre-formed header module, e.g. a connector header module or an electrode bearing header module, etc., to a hermetically sealed enclosure of the implantable medical device, typically including electronic integrated circuits, batteries, electromechanical pumps, or the like, are disclosed. A plurality of upstanding tabs that are fixed to the hermetically sealed enclosure, e.g. to the enclosure attachment surface, extend into a like plurality of tab channels formed in the header module housing. The upstanding tab(s) are inserted into the respective tab channel(s) during seating of the module and enclosure attachment surfaces and effects an initial alignment of the header module with the hermetically sealed enclosure. Each attachment tab has a retention feature formed on or in the tab that is designed to accommodate the flow of the thermoplastic material during the application of ultrasonic energy in the region of the tab channel and to cooperate with the solidified mass of thermoplastic material. During application of the ultrasonic energy, the thermoplastic material melts and flows into the remaining space of the tab channel and encapsulate the attachment tab including the retention feature. Upon termination of the ultrasonic energy, the thermoplastic housing material cools and solidifies and forms a continuous mass that encapsulates the surface of the attachment tab and the retention feature.

14 Claims, 11 Drawing Sheets

OTHER PUBLICATIONS

Ultrasonic Joining of Moulded Parts and Simi–Finished Parts of Thermo–Plastic Polymers in Mass Production: Forming with Ultrasound, Staking, Swaging and Tamping (Guideline DVS 2216, Part 3, 1992); Source: Welding in the World, Le Soudage Dams le Monde v 31 n 3 1993, pp. 205–207.

"Ultrasonic Assist in Drilling of Metals and in Molding of Polymer Powders", H.V. Fairbinks, Corporate Sourece: Wva University, Morgantown; Source: Proceedings of the International Conference on Production Engingeering, 27th, New Delhi, India, Aug. 27 through Sep. 4, 1977; Published by Institute of Eng. (India), Calcutta, 1977, v.2, p. 5, Publication Year 1977.

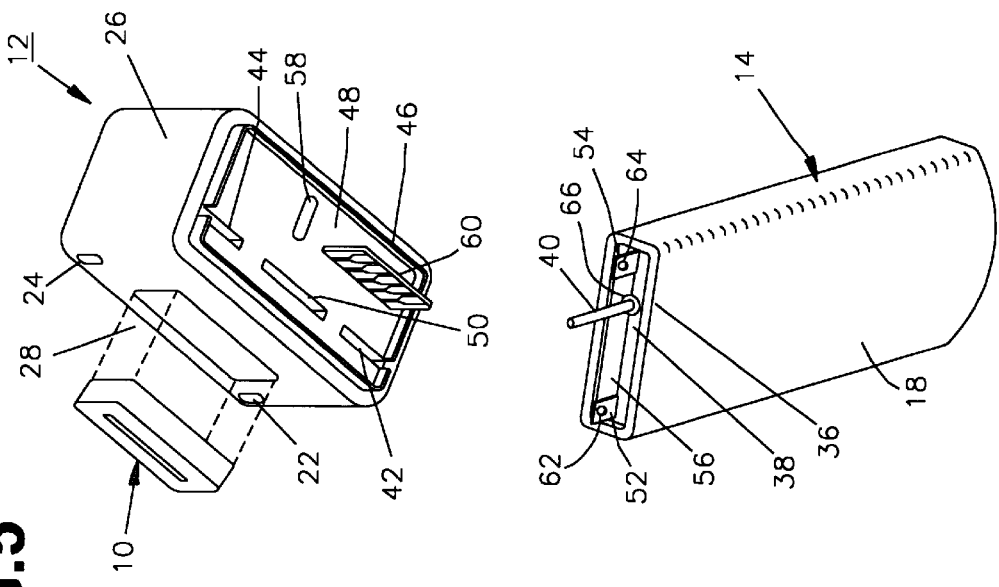
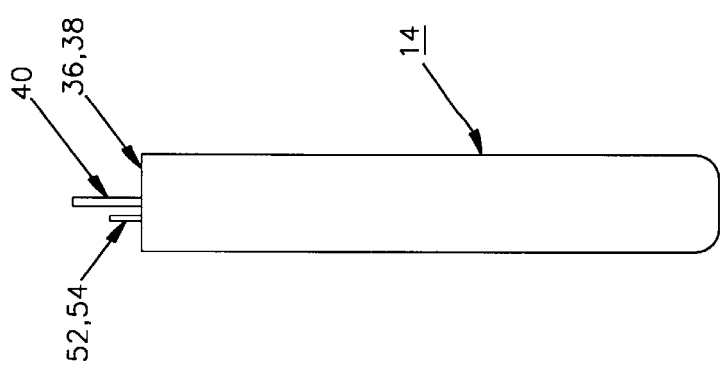
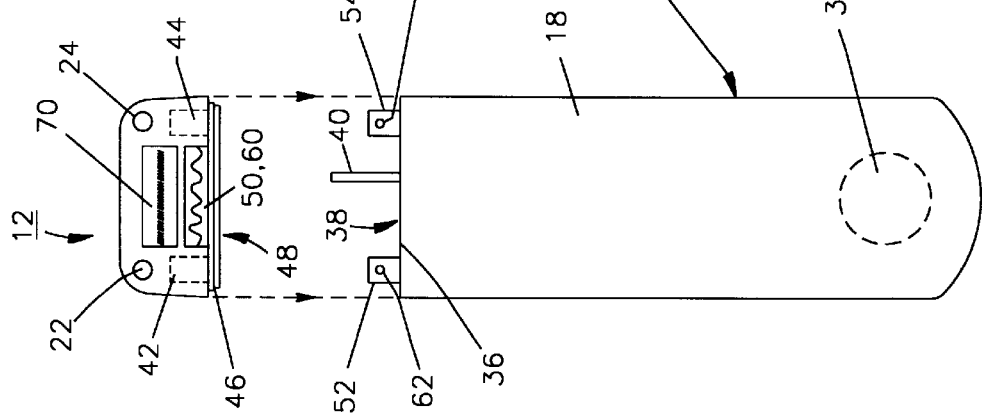

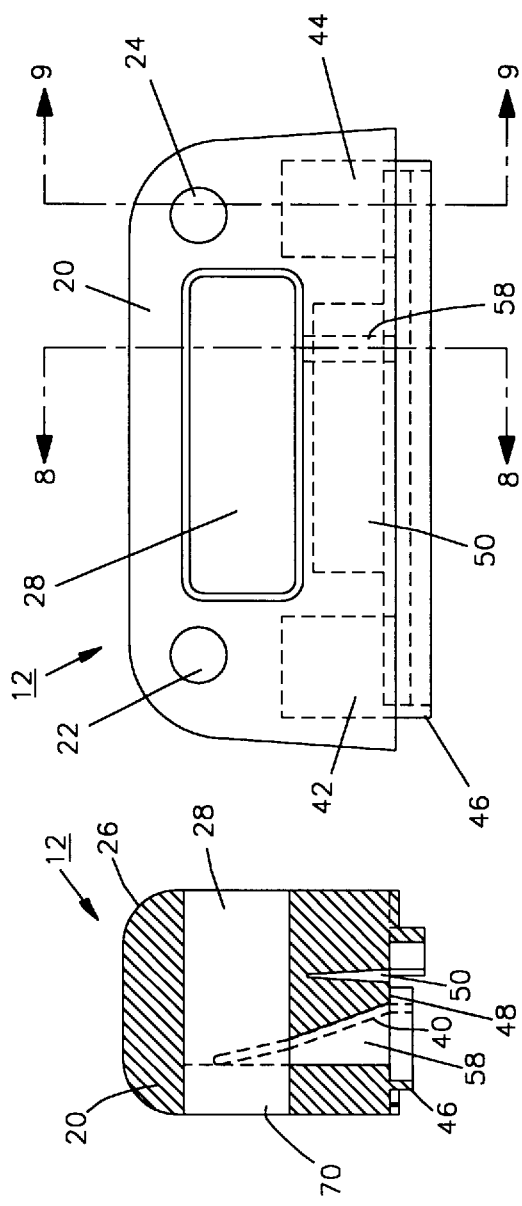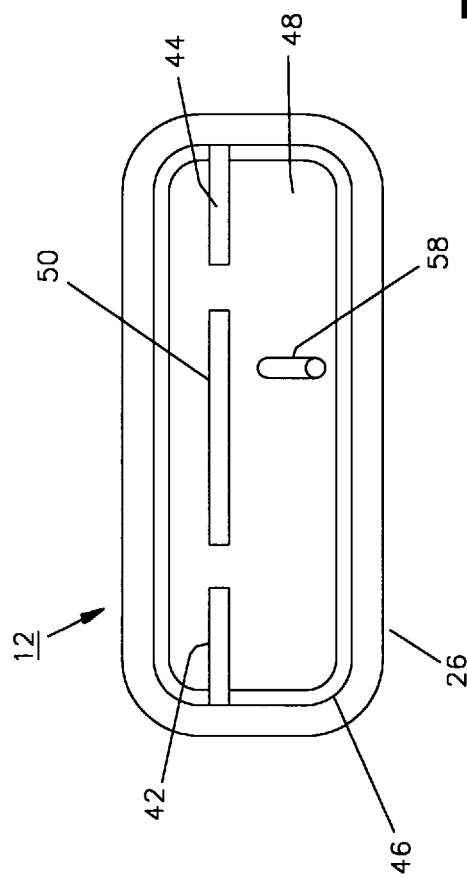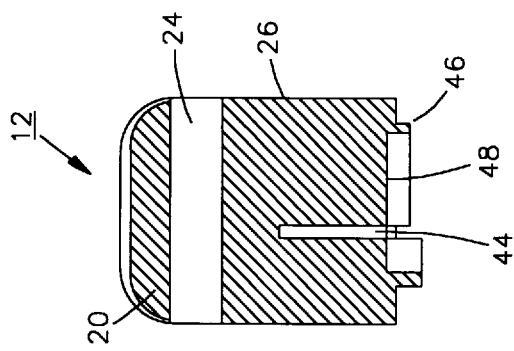

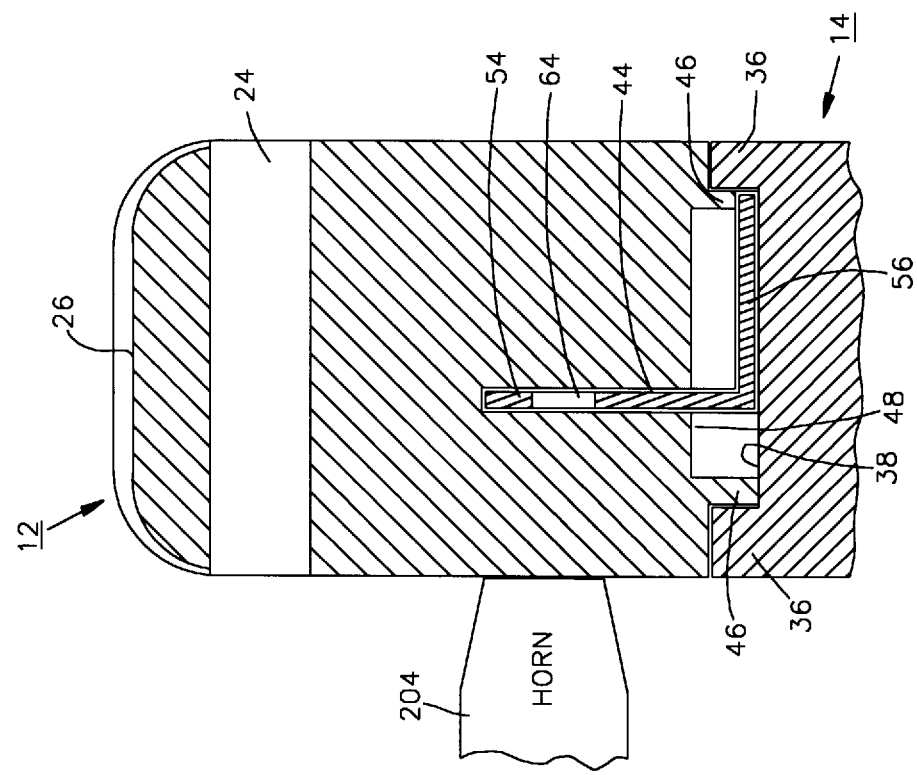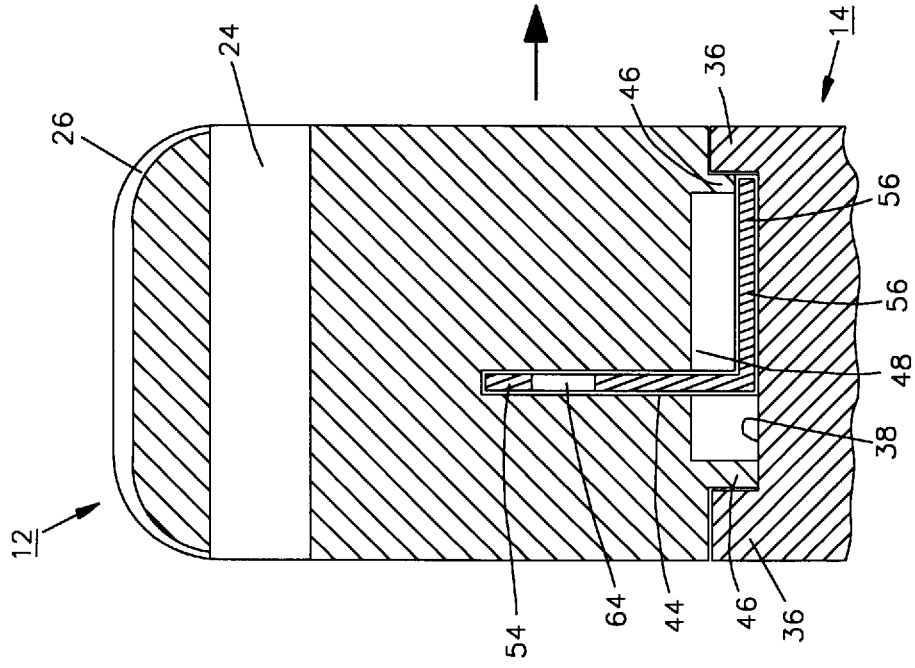

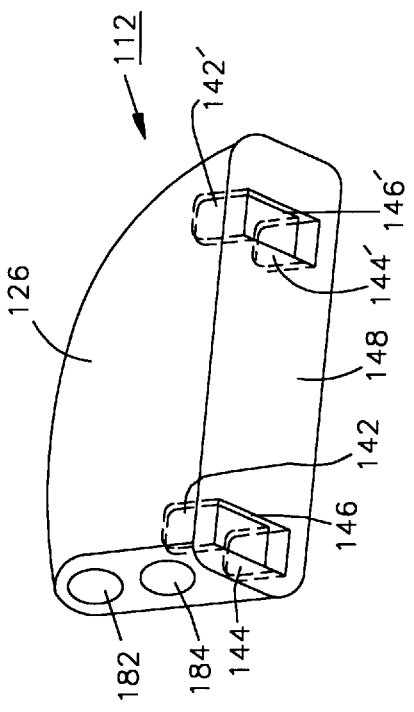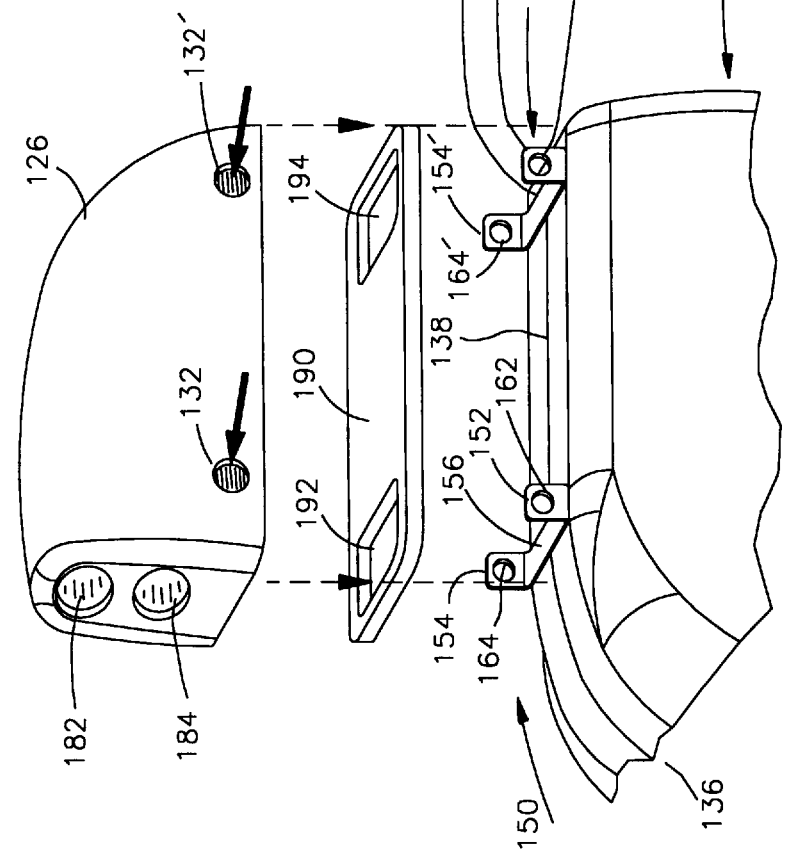

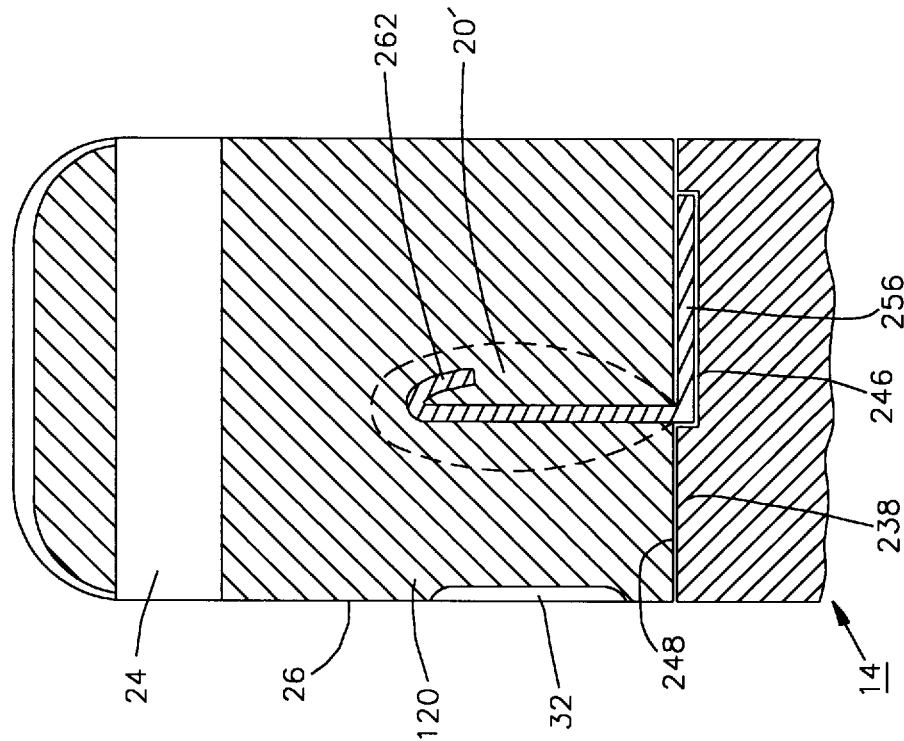
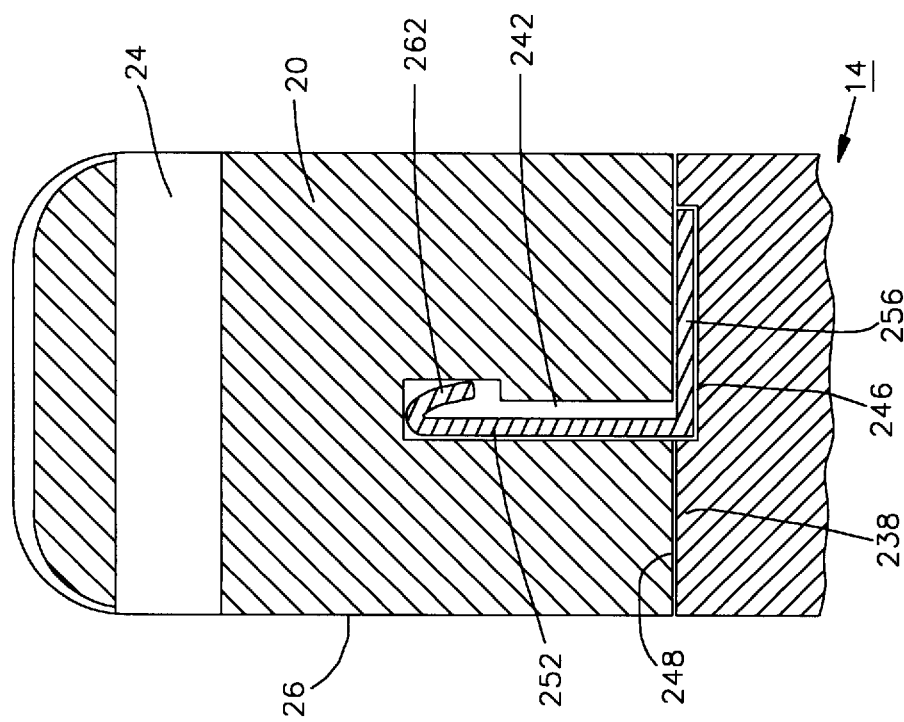

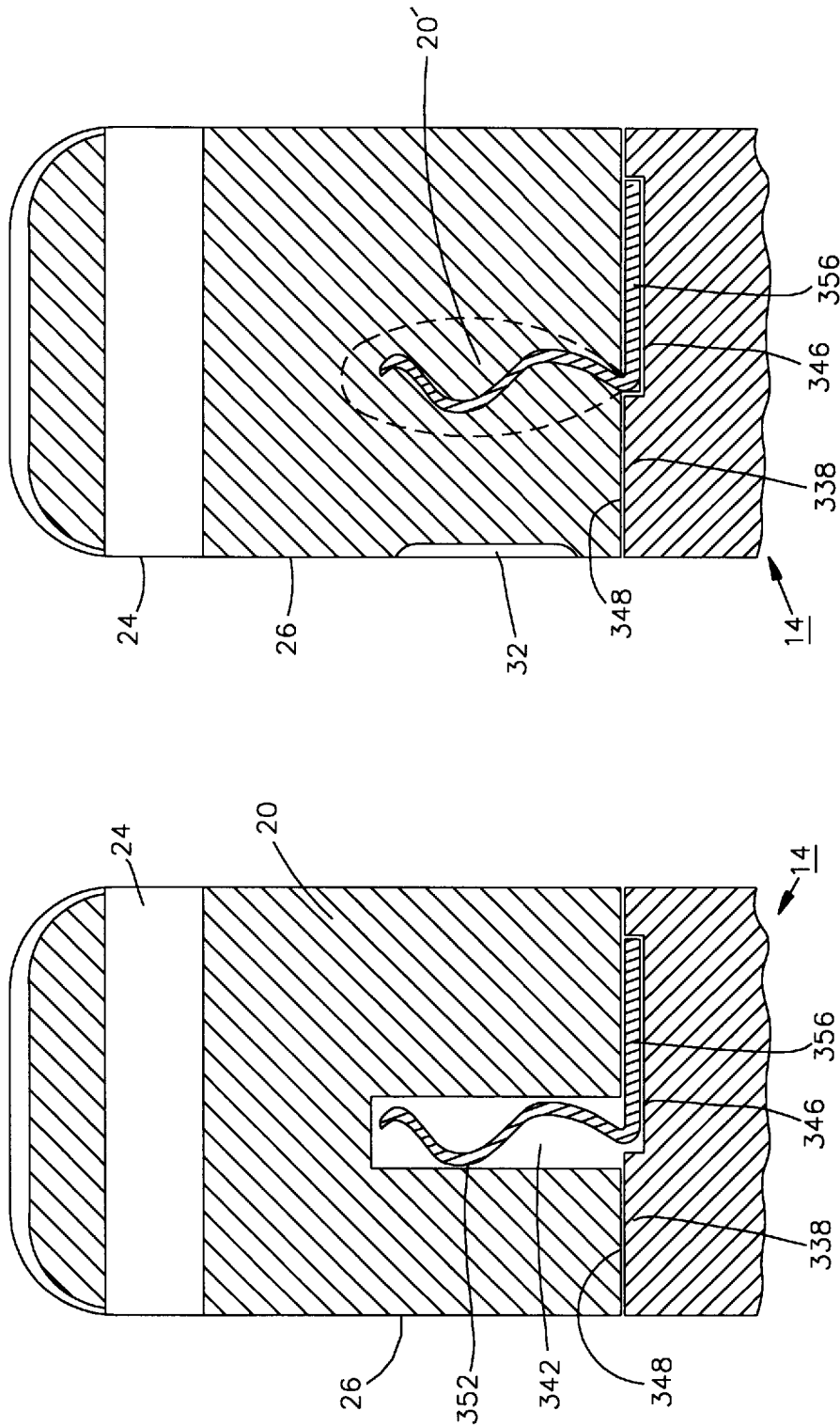

ATTACHMENT APPARATUS AND METHOD FOR AN IMPLANTABLE MEDICAL DEVICE EMPLOYING ULTRASONIC ENERGY

CROSS-REFERENCE TO RELATED APPLICATIONS

This application is a divisional application of U.S. patent application Ser. No. 08/904,601 filed Aug. 1, 1997 entitled "Attachment Apparatus and Method For An Implantable Medical Device Employing Ultrasonic Energy" to Wiklund et al. Reference is hereby made to commonly assigned, co-pending U.S. patent application Ser. No. (P-4797) filed Aug. 1, 1997, for ATTACHMENT APPARATUS AND METHOD FOR AN IMPLANTABLE MEDICAL DEVICE in the names of Eric Rieder et al.

FIELD OF THE INVENTION

The present invention generally relates to implantable medical devices and particularly to the attachment of a pre-formed header module, e.g. a lead or catheter connector header module or an electrode bearing header module, etc., to a hermetically sealed enclosure of the implantable medical device, typically including electronic integrated circuits, batteries, electromechanical pumps, or the like.

BACKGROUND OF THE INVENTION

The earliest implantable medical devices, e.g., implantable cardiac pacemakers and other body tissue stimulating devices, were formed of an implantable pulse generator (IPG) and a set of electrical leads attached between the IPG and heart or body tissue to be paced or stimulated. Typically, the IPG electrical circuit was powered either by Hg—Zn batteries or by induction of energy transmitted transcutaneously from a skin surface RF power generator and supplied electrical pacing or stimulating pulses to the leads. The IPG batteries and circuits were encapsulated within an epoxy compound partly for ease of manufacture and to allow hydrogen emitted by the Hg—Zn batteries to escape. Electrical connector pins and rings, if present, were initially permanently attached to the circuits. Other early implantable medical devices, e.g. implantable monitors and cochlear implants or the like were also formed in somewhat the same manner.

Such early implantable cardiac pacemakers suffered very short useful lives due to moisture ingress through the epoxy and causing electrical dendritic growth across, and shorting of, adjacent points of the circuit, battery terminals, or discrete transistor terminals. In addition, pacing leads frequently failed due to conductor stress fractures, and batteries depleted prematurely for a variety of reasons.

In the 1960's, IPG connector assemblies were formed integrally with other IPG circuit components and embedded in an epoxy housing to enable attachment of a chosen lead to the IPG circuit for initial implant or defective lead replacement purposes. These integrally formed connector assemblies typically comprised at least one metal, electrical connector block encapsulated therein that were aligned in relation to an elongated lead end receptacle for receiving the proximal lead end. Each connector block was formed to have a bore to receive the lead connector pin or ring, depending on the type of lead intended to be used, and a threaded cross bore receiving a trapped set screw. The connector block(s) was electrically directly attached to the IPG circuit. A silicone rubber suture boot was placed in the mold so that it's bore would be aligned with the elongated receptacle. The entire IPG including these connector assembly components, was then encapsulated in epoxy.

In use, the proximal lead connector end(s) was inserted into the appropriate lead connector receptacle until the lead connector pin or ring was received in the bore of the connector block(s). Then, the set screw was tightened by a hex wrench to maintain the firm electrical and mechanical attachment, and the opening through the molded epoxy housing to access the set screw was sealed. Sutures were tied around the suture boot(s) to seal it against the lead body.

Since about the mid-1970's, hermetically sealed, lithium batteries and miniaturized, digital and analog, integrated circuits (ICs) have been used in implantable medical devices, particularly for implantable cardiac pacemaker and nerve stimulation IPGs. The ICs, batteries, and other components are enclosed in hermetically sealed metallic enclosures or "cans" separated from the connector assembly components. Electrical connection with the connector block(s) and/or other components of the connector assembly is obtained by use of electrical feedthroughs supporting feedthrough pins that extend through the hermetically sealed can.

In certain instances, the lead connector assembly components external to the hermetically sealed enclosure are still to this date attached to an attachment surface thereof using an in situ molding process to seal the connector assembly components and form the receptacle for a lead or catheter proximal end, etc. Very simply, in the formation of a lead connector assembly for a cardiac pacemaker IPG, for example, the connector block(s) and feedthrough pin(s) are welded together and laid out in a mold with respect to any other associated components and mold plugs. An encapsulating compound is injected into the mold to form the connector header assembly molded to the IPG attachment surface as described, for example, in U.S. Pat. No. 4,041,956. This approach is time consuming and not terribly precise. If the resulting connector header assembly fails to meet dimensional tolerances or other quality requirements, it is difficult to rework the IPG.

In 1979, the MEDTRONIC® SPECTRAX® cardiac pacemaker IPGs were introduced having the digital and analog or hybrid IC's and lithium batteries forming the pacing circuit enclosed within a hermetically sealed titanium enclosure having feedthroughs extending through an enclosure attachment surface thereof. Such an assembly of these components is disclosed in commonly assigned U.S. Pat. Nos. 4,142,532 and 4,182,345, incorporated herein by reference.

The lead connector assembly, in this case and as used in IPG models to the present time by Medtronic, Inc., is manufactured as a separate pre-formed connector header module that encloses connector components and is attached to an enclosure attachment surface of the hermetically sealed enclosure and to the feedthrough pins. The connector header module is molded of a thermoplastic elastomer, e.g., a medical grade polyurethane, with an outer module surface and a number of receptacles and channels within it that in some instances are accessible through windows extending to the module surface. The connector header module receives the electrical connector block(s) in connector block receptacle(s) such that the connector block bore(s) is aligned with elongated lead connector receptacle(s) for receiving the proximal lead connector end assembly(s). In the typical design, each such connector block is formed with a threaded cross bore receiving a trapped set screw as described above. Each set screw of each connector block in a connector block receptacle is also aligned with a septum receptacle for receiving a silicone rubber set screw septum. The preformed connector header module is formed with pin channel (s) for directing the feedthrough pin(s) into contact with the respective connector block(s) and with window(s) to allow the connector block(s) and septum(s) to be inserted into their respective receptacle(s). In each case, the connector block receptacle window or a further window to the module surface is provided for allowing the feedthrough pin end to be welded to the connector block. The windows(s) and pin channel(s) are typically back filled with a medical grade silicone adhesive after the welding step and attachment of the connector header module to the hermetically sealed enclosure.

To attain and maintain these characteristics, the receptacle for the connector block and the connector block itself are dimensioned within tight tolerances to precisely align the connector block bore with the lead connector receptacle. In one approach, the connector block receptacle opening dimensions are reduced and the opening edge shaped so that the connector block stretches the opening edge as it is inserted to be seated within the connector block receptacle. In certain other cardiac pacemaker IPGs, each connector block is inserted into a connector block receptacle and ultrasonic energy is applied to the edge of the connector block window to melt it over and tamp it against the exposed surface of the connector block. This ultrasonic tamping technique of dissimilar material parts is similar to that shown in the article entitled "Ultrasonic joining of moulded parts and semi-finished parts of thermo-plastic polymers in mass production—Forming with ultrasound. Staking, swaging and tamping (Guideline DVS 2216, Part 3, 1992)", *Welding in the World, Le Soudage Dans Le Monde,* Vol. 31, No. 3, pp. 205–207 (1993).

As a general rule, the connector header module formed as described above, has to satisfy very tight tolerances and remain dimensionally stable over a long time period of implantation within the hostile environment of the human body. Any substantial initial or time-induced misalignment of the lead connector receptacle bore(s) extending through the molded module housing and the connector block bore(s) can make initial attachment or removal and replacement of a lead connector end impossible or unreliable.

During the attachment of the connector header module to the hermetically sealed enclosure, medical grade adhesive may be employed to adhere the module attachment surface with the enclosure attachment surface. During the curing of the adhesive, it is necessary to ensure that the attachment surfaces are not disturbed. It has been proposed to employ mechanical attachment mechanisms as a substitute for or in addition to the use of the medical grade adhesive between the attachment surfaces to provide stability and strength. Such mechanical attachment mechanisms that have been proposed for use or actually used either alone or with adhesive take a variety of forms, e.g., the forms shown in commonly assigned U.S. Pat. Nos. 4,142,532 and 4,182,345, both incorporated herein by reference in their respective entireties. While these approaches have merit, they require use of additional, precision piece parts and assembly steps that can add to the cost and time spent in assembling the connector header module with the hermetically sealed enclosure.

In a further current approach employing both adhesive and temporary mechanical fixation, tab channels are formed in the connector header module to receive upstanding attachment tabs that are welded to the enclosure attachment surface to extend outward therefrom. The upstanding attachment tabs are formed with hooks at their ends that snap into engagement with undercuts that are intentionally formed in the tab channels. Adhesive is applied to the mating attachment surfaces and into the tab channels. This mechanical attachment provides a temporary fixation with relatively low resistance to dislodgement for several hours until adhesive applied to the mating attachment surfaces sets up.

Finally, it should be noted that it has been recently proposed to form the connector header module as part of a shroud surrounding and adhering to the rim of the hermetically sealed enclosure in order to simplify the assembly by reducing the number of parts, assembly steps and required tolerances. Such a configuration is shown in commonly assigned U.S. Pat. Nos. 5,535,097, 5,522,861, 5,456,698 and 5,431,695, all incorporated herein by reference in their respective entireties. In this configuration, the shroud is preferably formed of a flexible silicon rubber, and pacing leads may be attached and replaced in the normal manner for an implantable pacing system. However, the use of silicone rubber has its own disadvantages related to dimensional instability and lack of rigidity, general design aesthetics, and potential discoloration of the silicone rubber during storage and sterilization which contribute to lack of market acceptance.

The adhesion force or "peel and pull strength" of the connector header module with the hermetically sealed enclosure at the mating attachment surfaces is important both during the adhesive curing time and in later chronic implantation of the implantable medical device. The pull strength is the separation force, specified in pounds, applied perpendicularly to the plane of the header module and enclosure attachment surfaces sufficient to pull the header module away from the hermetically sealed enclosure. The peel strength is the separation force, specified in pounds, applied laterally against a major side of the header module sufficient to break the attachment laterally. The curing or drying of adhesive between the mating attachment surfaces to establish a specified peel and pull strength takes time, and this delay in manufacturing is undesirable. Moreover, the peel and pull strength that can be achieved is limited by the areas of contact of the mating attachment surfaces. Consequently, a need remains for an improved mechanical attachment mechanism and method that avoids undue delay and provides enhanced peel and pull strength upon completing the attachment. As will become apparent from the following, the present invention satisfies that need.

Certain implantable medical devices other than IPGs also require the attachment of a pre-formed header module with a hermetically sealed enclosure. Such pre-formed header modules do not include lead connector components and connector end receptacles. Similar considerations of simplified manufacture, reduced cost and enhanced peel and pull strength also apply to the assembly of such pre-formed header modules and hermetically sealed enclosures.

SUMMARY OF THE INVENTION

It is an object of the present invention to solve these problems identified with prior art methods and mechanisms for attaching a pre-formed header module to a hermetically sealed enclosure of an implantable medical device.

A number of advantages are achieved in the practice of the present invention. A mechanical attachment is effected quickly and reliably employing a simple retention structure and minimal attachment steps that may be readily automated. The retention structure employs a minimal number of parts all of which are found either attached to the hermetically sealed enclosure or in the header module. Therefore the retention structure and method does not require the use of any additional parts or materials that must be combined with or attached to either of these major parts. The retention structure self aligns and ensures that the pre-formed header module is aligned precisely to the hermetically sealed enclosure prior to and during the completion of the retention steps. A relatively tight dimensional specification can be defined for the seating and alignment of the header module with the hermetically sealed enclosure, which results in a more dimensionally uniform and attractive finished product. A relatively high peel and pull strength is achieved Immediately following the mechanical attachment steps. The high peel and pull strength can be realized with a minimal size of the retention structure which is important to the desirable miniaturization of the implantable medical device The use of adhesives that require a relatively long cure time is eliminated, thereby reducing assembly steps and materials and shortening assembly time and cost. Adhesive attachment can be combined with the mechanical attachment for sealing and isolation purposes and to increase the peel and pull strength of the attachment bond. If adhesive is used, the mechanically attached header module and hermetically sealed enclosure assembly can still be handled during the adhesive drying time without a significant risk that they will become mis-aligned or separated before the adhesive dries. The mechanical attachment is immediately secure and does not require a long curing time of an adhesive. To the extent an adhesive is employed, a relatively viscous body implantable grade adhesive may be employed to cushion the interface space between the mating module and enclosure attachment surfaces and seal any channels thereto. In this way, irregularities in the mating attachment surfaces and internal channels and spaces within the header module housing can be filled.

These advantages are realized in a retention structure that preferably comprises at least one and preferably a plurality of upstanding tabs that are fixed to the hermetically sealed enclosure, e.g. to the enclosure attachment surface, and extend into a like number of tab channels formed in the header module housing. The insertion of the upstanding tab(s) into the tab channel(s) during seating of the module and enclosure attachment surfaces effects an initial alignment of the header module with the hermetically sealed enclosure. Each attachment tab has a retention feature formed on or in the tab that is designed to accommodate the flow of the thermoplastic material during the application of ultrasonic energy in the region of the tab channel and cooperate with the solidified mass of thermoplastic material. During application of the ultrasonic energy, the thermoplastic material melts and flows into the tab channel and encapsulate the attachment tab including the retention feature. Upon termination of the ultrasonic energy, the thermoplastic housing material cools and solidifies and forms a continuous mass that encapsulates the surface of the attachment tab and the retention feature. The retention feature preferably accommodates a lateral thermoplastic material flow, with respect to the direction the attachment tab is extending, across or through a recess or retention hole forming a retention portion of the attachment tab. In the preferred embodiment, the retention feature is a simple tab hole or holes extending through the attachment tab through which the melted thermoplastic material flow and forms a continuous mass upon cooling and solidification. The resulting peel and pull strengths following solidification and cooling of the thermoplastic material around or through the retention feature and the attachment tab surface is significantly higher than the prevailing specified minimum values. In this manner, the advantages summarized above are realized without the use of any adhesive. However, the retention structure and method is usable with adhesives and/or a cushioning spacer inserted into the space between the enclosure and module attachment surfaces.

BRIEF DESCRIPTION OF THE DRAWINGS

These and other objects, advantages and features of the present invention will be appreciated as the same becomes better understood by reference to the following detailed description of the preferred embodiment of the invention when considered in connection with the accompanying drawings, in which like reference numbers designate like parts throughout the figures thereof, and wherein:

FIG. 2 is an exploded plan view of the header module in relation to the hermetically sealed enclosure of the implantable cardiac monitor of FIG. 1;

FIG. 3 is a side view of the hermetically sealed enclosure of the implantable cardiac monitor of FIG. 1;

FIG. 4 is an isometric view toward the attachment surface of the hermetically sealed enclosure of the implantable cardiac monitor of FIG. 1;

FIG. 5 is an exploded isometric view toward the attachment surface of the pre-formed header module of the implantable cardiac monitor of FIG. 1;

FIG. 6 is an elevation plan view of the header module of the implantable cardiac monitor of FIG. 1;

FIG. 7 is an attachment surface plan view of the header module of the implantable cardiac monitor of FIG. 1;

FIG. 8 is a side cross-section view of the header module of FIG. 6 taken along lines A—A;

FIG. 9 is a side cross-section view of the header module of FIG. 6 taken along lines B—B;

FIG. 12 is a partial side cross-section view of the header module and hermetically sealed enclosure taken along lines 11—11 of FIG. 10 showing the location of the upstanding attachment tab in a respective tab channel in the connector header module;

FIG. 13 is a partial side cross-section view of the header module and hermetically sealed enclosure taken along lines 11—11 of FIG. 10 showing the location of the upstanding attachment tab in a respective tab channel in the connector header module and the advancement of the ultrasonic head tool against the module housing surface in the system of FIG. 11;

FIG. 16 is a simplified partial exploded isometric view of the connector header module in relation to a pre-form gasket and a set of four upstanding tabs extending upward from the IPG hermetically sealed enclosure housing attachment surface for attachment in the manner depicted in FIGS. 11–14;

FIG. 17 is a perspective view of the module attachment surface of the connector header module of FIG. 16;

FIGS. 18 and 19 are side cross-section views of an alternative retention feature of the upstanding attachment tabs that may be employed in lieu of the tab hole retention feature; and FIGS. 20 and 21 are side cross-section views of a further alternative retention feature of the upstanding attachment tabs that may be employed in lieu of the tab hole retention feature.

Figure 1:
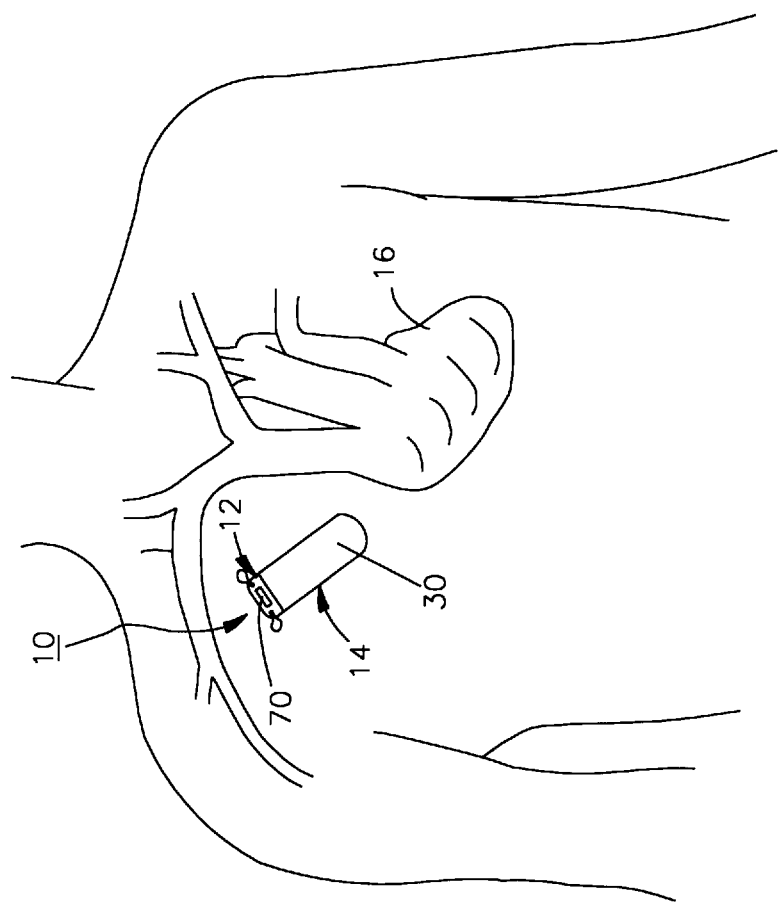
FIG. 1 is a simplified schematic view of an implantable cardiac signal monitor embodying the improved attachment of a pre-formed header module to a hermetically sealed enclosure in accordance with the present invention implanted in relation to a human heart.

The drawing figures are not all necessarily to scale.

DETAILED DESCRIPTION OF THE PREFERRED EMBODIMENTS

The preferred embodiments relate to use of the mechanism and method summarized above to attach a pre-formed header module attachment surface with a hermetically sealed enclosure attachment surface in the manufacture of an implantable medical device. Such implantable medical devices include implantable drug dispensers, IPGs (including cardiac pacemakers, pacemaker-cardioverter-defibrillators, nerve, muscle and neurological stimulators, cardiomyostimulators, etc.), implantable cardiac signal monitors and recorders and the like. Virtually all MEDTRONIC® electronic implantable medical devices that require attachment of a hermetically sealed power supply and circuitry with an interchangeable catheter or electrical lead or the like employ such a general configuration of a hermetically sealed enclosure and a pre-formed header module thereto.

In a first illustrated preferred embodiment, the attachment mechanism and method is used to attach a cardiac signal sense electrode bearing header module to a hermetically sealed cardiac signal monitor. In a further illustrated embodiment, the attachment mechanism and method are used to attach an IPG connector header module to a hermetically sealed enclosure of an IPG of the types listed above. At least in the case of IPGs and cardiac signal monitors, electrical feedthroughs extending through the hermetically sealed enclosure are coupled with components in the header module.

The attachment method and mechanism may also be used to attach an implantable drug pump catheter connector, header module to the hermetically sealed enclosure for the pump mechanism, battery and ICs controlling the pumping operation. However, those of skill in the art will be readily able to adapt the teachings found herein to other implantable medical devices. It will be understood that the term "header module" as used in the description and claims is comprehensive of any such pre-formed header module, including the electrode bearing header module of the first embodiment and the lead connector header module of the second embodiment FIG. 1 is a simplified schematic view of an implantable cardiac signal monitor 10 embodying the improved attachment of a pre-formed header module 12 to a hermetically sealed enclosure 14 in accordance with the first preferred embodiment of the present invention implanted in relation to a human heart 16. The cardiac signal monitor 10 includes at least header and can sense electrodes 70 and 30 across which electrical signals attendant to the depolarization and re-polarization of the heart 16 are sensed. The electrical circuitry within the cardiac signal monitor samples and records this electrogram of the heart over a number of heart cycles. The cardiac signal monitor 10 is sutured to subcutaneous tissue at a desired orientation of the electrodes 70 and 30 to the axis of the heart to detect and record the EGM for subsequent uplink telemetry transmission to an external programmer (not shown). FIG. 1 shows only one such orientation and is not necessarily to scale.

In general, the hermetically sealed enclosure 14 includes a lithium battery, circuitry that controls device operations and records arrhythmic EGM episodes, and a telemetry transceiver antenna and circuit that receives downlink telemetry commands from and transmits stored data in a telemetry uplink to the external programmer. The circuitry and memory may be implemented in discrete logic or a microcomputer based system with A/D conversion of sampled EGM amplitude values. The particular features and operations of the cardiac signal monitor are not of importance to the present invention. One exemplary operating system is described in commonly assigned, co-pending U.S. patent application Ser. No. 08/678,219, filed Jul. 11, 1996, for MINIMALLY INVASIVE IMPLANTABLE DEVICE FOR MONITORING PHYSIOLOGIC EVENTS, incorporated herein by reference.

This preferred embodiment involves the retention method and apparatus for attaching the pre-formed header module 12 to the hermetically sealed enclosure 14 at respective attachment surfaces thereof and providing electrical connection between the header electrode 20 and the EGM recording circuitry. FIG. 2 is an exploded plan view of the header module 12 in relation to the hermetically sealed enclosure 14. FIGS. 3 and 4 show the hermetically sealed enclosure 14 in side and isometric views. The hermetically sealed enclosure 14 is formed of an elongated and relatively flat metallic can 18 having a can lid formed across the end thereof and providing the hermetic enclosure attachment surface 38 bounded by a can and lid weld rim 36 extending around the respective peripheries thereof. An electrical feedthrough 66 is welded into the hermetic enclosure attachment surface 38 so that an electrically isolated feedthrough pin 40 extends across and outwardly therefrom.

It will be understood that the telemetry antenna, electrical circuitry and battery described above in general terms are mounted into a sub-assembly with appropriate insulators, spacers and circuit connections already made that is to be inserted into the can 18 and attached to the internally extending feedthrough pin 40. The sub-assembly is inserted into the can 18 and the can lid is welded to the can opening around the lid weld rim 36 to hermetically seal the components within the hermetically sealed enclosure 14.

Figure 10:
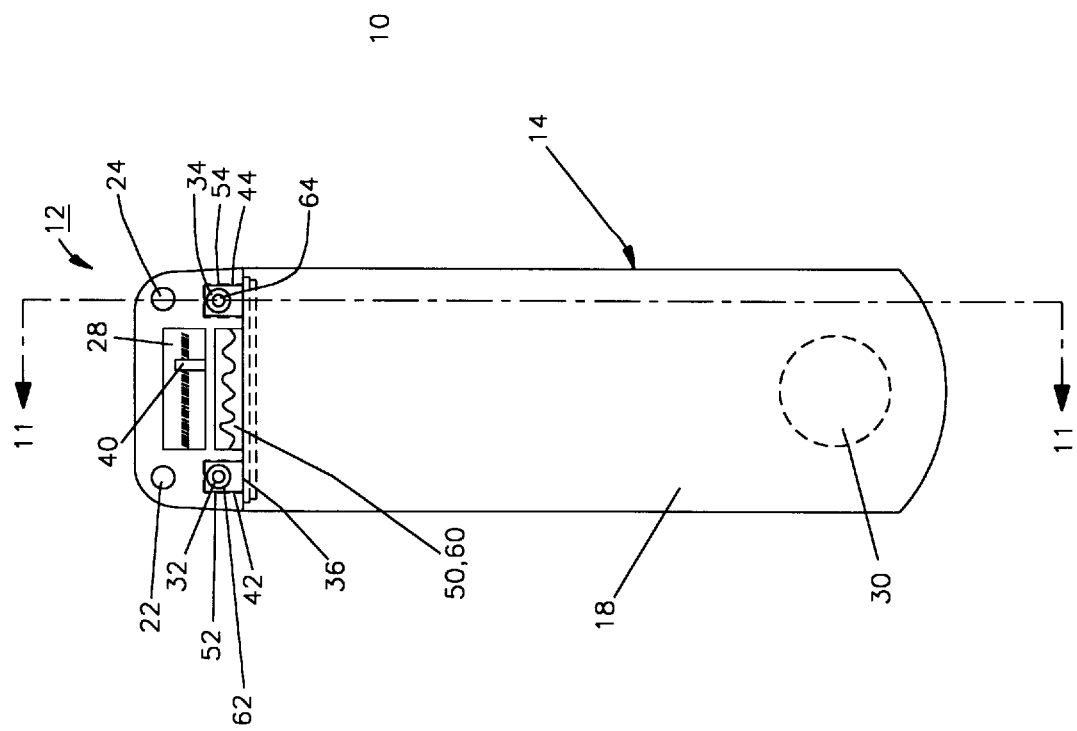
FIG. 10 is an elevation plan view of the seating of the header module attachment surface against the hermetically sealed enclosure attachment surface following the assembly of the implantable cardiac monitor of FIG. 1.

The cardiac signal monitor 10 includes a can electrode 30 formed by all or part of the exterior surface of metallic can 18 and at least one further header electrode 70 formed in the header module 12. The metallic can 18 and the further electrode 70 are electrically connected to sense amplifier circuit input terminals. The metallic can 18 can either be totally un-insulated so that the entire exterior surface operates as can electrode 30 or can be insulated in a pattern leaving a portion exposed as the can electrode 30 as shown in FIGS. 2 and 10.

Upstanding attachment tabs 52 and 54, having tab holes 62 and 64, respectively, formed therein, extend outward of the can lid from opposite ends of a tab base 56. Tab base 56 is welded at a predetermined location to the can lid and provides part of the enclosure attachment surface 38 within the lid weld rim 36. As shown in FIGS. 2–4, the upstanding attachment tabs 52 and 54 are in line with one another and spaced apart from the upstanding feedthrough wire 40 in a predetermined manner that dimensionally corresponds to tab channels formed in the header module housing 20. In accordance with the present invention the tab holes 62, 64 are employed as one form of a retention feature through which the thermoplastic material of the module housing 20 flows during application of ultrasonic energy and solidifies as described below.

Figure 14:
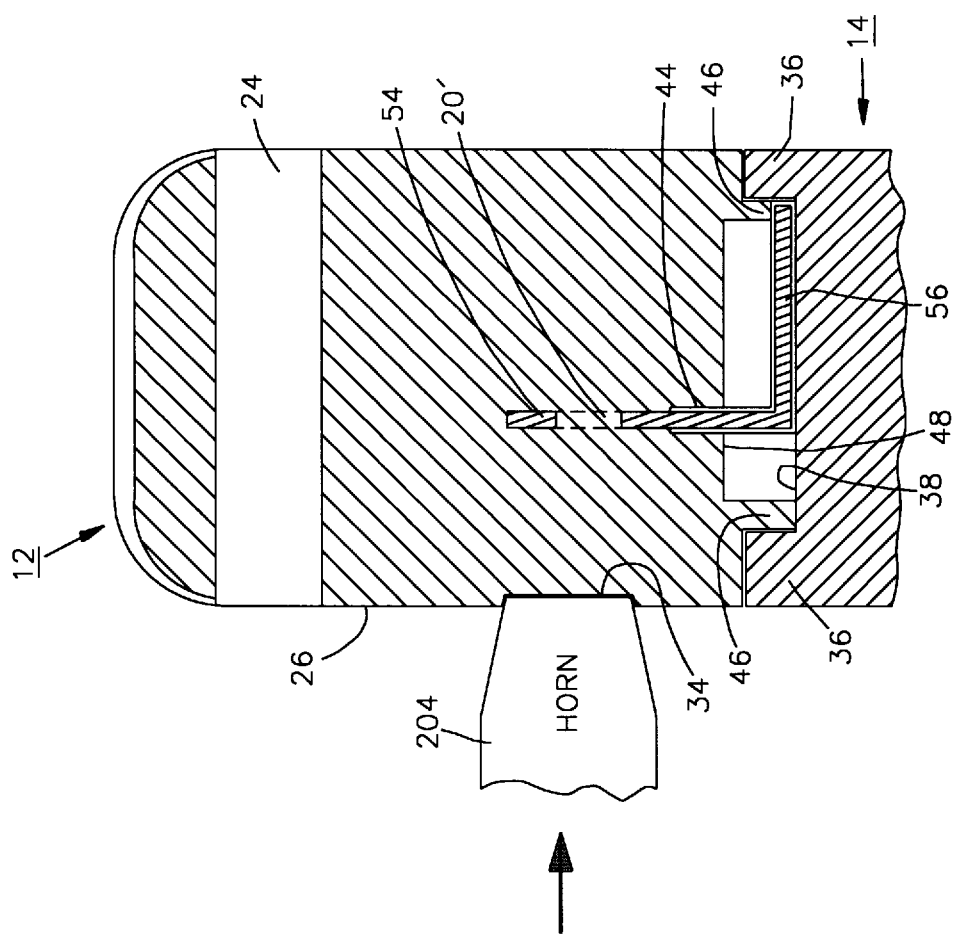
FIG. 14 is a partial side cross-section view of the header module and hermetically sealed enclosure taken along lines 11—11 of FIG. 10 showing the application of ultrasonic energy melting the thermoplastic housing material around upstanding attachment tab and advancement of the ultrasonic head tool into the module housing surface.

The header module 12 is molded of a rigid thermoplastic, e.g., a medical grade polyurethane, housing 20 having an exposed module surface 26 and a number of receptacles and channels shown in greater detail in FIGS. 6–9. Components including a header electrode 70 and radiopaque ID plate 60 fitted within respective electrode channel 28 and plate channel 50 of the housing 20 are shown in FIGS. 2, 5 and 10. FIGS. 10–14 show how the header module 12 is attached to the hermetically sealed enclosure 14 employing ultrasonic energy to melt the thermoplastic material to flow around the retention features of the upstanding tabs 52 and 54. FIG. 14 shows a mass 76 of the thermoplastic housing material that has melted due to the applied ultrasonic energy filling the space between the upstanding tab and the tab channel and extending through the tab hole retention feature in the final assembly step.

The header module housing 20 is molded to have a pair of transversely extending suture bores or holes 22 and 24 extending across the width thereof through which sutures are passed into adjacent subcutaneous tissue when the cardiac signal monitor 10 is implanted as shown in FIG. 1. The suture holes 22 and 24 allow the electrodes 70 and 30 of the cardiac signal monitor 10 to be oriented at any desired angle to the heart.

An electrode channel 28 is formed extending transversely across the header module housing 20 located generally between the suture bores 22 and 24. The electrode channel 28 receives an electrode plate 70 inserted therein (in the broken line location designated 70' in FIG. 8) from one side opening so that an exposed electrode surface appears in a window on the other side of the header module housing 20. A pin receiving channel 58 is formed extending upward from module attachment surface 48 to intersect with the transverse electrode channel 28.

Upon assembly of the header module 12 with the hermetically sealed enclosure 14 shown in FIG. 10, the feedthrough pin 40 is directed through the pin receiving channel 58 and deflected at an angle that intersects the interior surface of the electrode plate 70 as shown in the broken line deflection path 40' in FIG. 8. Then, in manufacture, the terminus of the feedthrough pin 40 can be welded to the interior surface of the electrode plate 70 through the electrode channel 28. Finally, the electrode channel 28 can be back filled with a spacer and adhesive or simply with a medical grade silicone adhesive typically used in implantable medical devices.

In this particular embodiment, the module attachment surface 48 is bounded by a downwardly extending module rim 46 that fits within the lid weld rim 36 when the header module 12 is fitted onto the hermetically sealed enclosure 14 as shown in FIGS. 4–9. In that assembly depicted in FIG. 10, the module rim 46 spaces the module attachment surface 48 from the enclosure attachment surface 38 by a certain amount. The module rim 46 can be used in cooperation with weld rim 36 as an adhesive dam to receive adhesive or a pre-formed compressible gasket placed into the space between the module attachment surface 48 and the enclosure attachment surface 38.

In accordance with the present invention, it is not absolutely necessary to have such a module rim 46 and pronounced space or to employ adhesive to fill this space. An alternative surface configuration minimizing the space is depicted in FIGS. 19–21 and described below. The space is desirably minimized to the extent that it is possible to do so by molding the module attachment surface 48 in a complementary pattern to the topography of the enclosure attachment surface 38. Due to manufacturing variances, gaps will likely remain that can be filled with a thin layer of adhesive or with the pre-formed gasket prior to seating the module attachment surface 48 against the enclosure attachment surface 38.

A pair of upwardly extending tab channels 42 and 44 are formed in the header module housing 20 that extend upward from the module attachment surface 48 in locations that are aligned with the locations of the upwardly extending attachment tabs 52 and 54, respectively, as shown in FIGS. 4–9. The tab channels 42 and 44 are shaped in height, width and thickness to receive the attachment tabs 52 and 54 when the header module 12 is seated against the hermetically sealed enclosure 14 as shown in FIG. 10.

FIG. 10 shows the completed implantable cardiac monitor after attachment of the header module 12 to the hermetically sealed enclosure 14. The upstanding attachment tabs 52 and 54 and the bore holes 62 and 64, respectively, can be seen through the transparent thermoplastic material forming the module housing 20. Slight horn depressions 32 and 34 are formed in the defined locations of the housing surface where a circular ultrasonic horn face was applied in the application of the ultrasonic energy in the manner described below in reference to FIGS. 11–14.

FIGS. 11–14 depict an ultrasonic welding system and the manufacturing steps of attaching the pre-formed header module 12 to the enclosure attachment surface 38 of the hermetically sealed enclosure 14 using ultrasonic energy. The depicted attachment steps follow the assembly and welding of the hermetically sealed enclosure 12 to its lid and the attachment of the tab base 56 to the lid to form the enclosure attachment surface 38 as described above. Moreover, the radiopaque ID plate 60 is fitted into the plate channel 50, and the header electrode 70 is fitted into the position 70' of the electrode channel 28. The illustrated attachment steps can either follow or preferably precede the attachment of the terminus of the feedthrough pin 40 to the interior surface of the header electrode 70 and the back fill of the electrode channel 28.

The system of FIG. 10 is similar to that shown in the article "Ultrasonic pressing of plastic-film capacitor" by S. Kaneko et al., in *Ultrasonics International* 93 *Conference Proceedings,* (1993) pp. 699–702 and is representative of a computerized ultrasonic welding system sold by Branson Sonic Power Co. (Danbury, Conn. The ultrasonic welding system 200 includes the control circuit 202 that operates the ultrasonic horn 204 to apply ultrasonic welding energy to the header module 12 under the control of a microprocessor based work station 206 that is used by the human operator. The human operator enters an applied static force value, a linear travel distance, the ultrasonic weld time, and a cooling time following the ultrasonic weld time. The operator may select the amplitude of the ultrasonic vibrations of the ultrasonic horn 204 and the ultrasonic frequency, although these may be fixed for each weld cycle of a given configuration of ultrasonic horn 204 and header module 12.

The vibration amplitude and frequency, the applied static force, and the time that the ultrasonic vibrations of the horn 204 are applied to the surface of the header module 12 are factors that contribute to the ultrasonic power that is delivered. When the ultrasonic power is delivered, the ultrasonic energy converts contact between the horn surface and the adjacent thermoplastic material into heat energy that melts the thermoplastic material. In the preferred embodiments, the ultrasonic energy melts a mass of the thermoplastic material extending from the horn surface laterally to the tab channel. The volume and depth of the melted mass is also controlled as a function of the shape and surface area of the horn surface of ultrasonic horn 204 and the depth to which it penetrates into the surface 26 of the header module housing 20 as shown in FIGS. 14, 19 and 21. As the horn surface penetrates into the surface, it moves closer to the upstanding tab channel and the upstanding tab therein as the thermoplastic material melts. The area of melt then advances into the tab channel to melt a mass of the thermoplastic material around the retention feature of the upstanding tab. It is desirable to control the depth of penetration to ensure that the horn surface does not reach the upstanding tab and convey ultrasonic energy directly down it to the hermetically sealed enclosure. Therefore, the linear travel of the horn 204 is set to the dimensions of the particular header module 12 so that the applied ultrasonic energy is concentrated in the region surrounding the tab channels to melt the adjoining thermoplastic material to flow around at least a tab free end portion of the attachment tab including the retention feature therein.

These entered ultrasonic weld cycle values are translated into operating commands by the work station 206 that are conveyed on bus 232 to the control circuit 202. The work station 202 may also supply commands to control the adjustment of the work piece holder 208 and horn 204 to successively locate each upstanding tab and tab channel with respect to the horn surface for each ultrasonic weld cycle.

Figure 11:
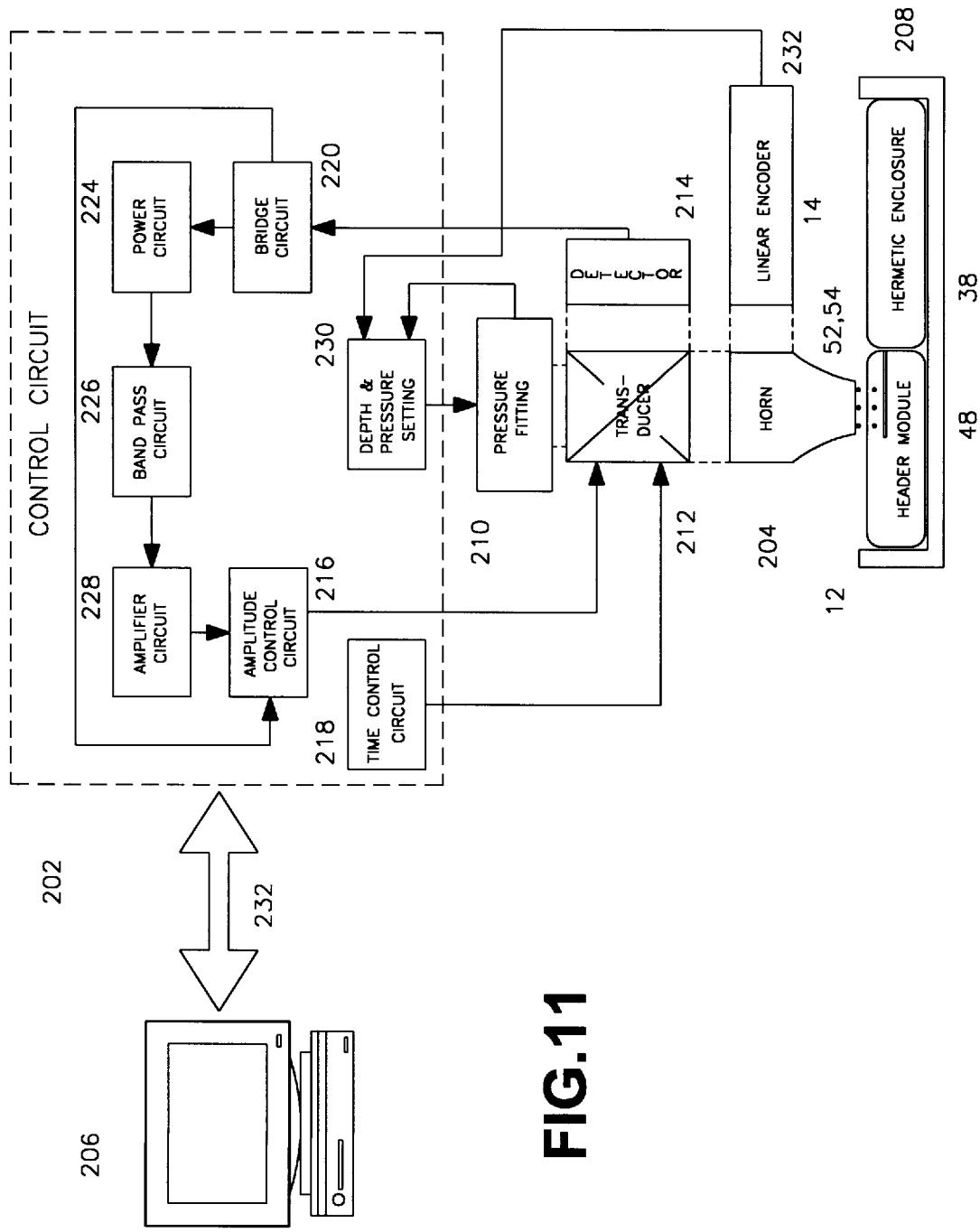
FIG. 11 is a simplified system block diagram for employing ultrasonic welding energy in the attachment of a header module to a hermetically sealed enclosure in accordance wit the method of he invention.

In the weld operating cycle, the header module 12 and the hermetically sealed enclosure 14 are seated together as shown in FIGS. 10 and 12 and fitted into a work piece holder 208 adjacent the ultrasonic horn 204 as shown in FIG. 11. The contact of the horn surface with the exterior surface of the header module 12 is established. The ultrasonic horn 204 is mounted to a pressure fitting 210 that is controlled by a pressure setting circuit 230 to apply a precisely controlled static force of the horn end surface against the outer surface 26 of the header module 12 at the defined header surface location. An emitter or transducer 212 is coupled between the pressure fitting 210 and the ultrasonic horn 204 that vibrates the horn 204 at the ultrasonic frequency and amplitude and for a time set by the time control circuit 218. At the expiration of the ultrasonic time, a further cooling time is prescribed before the horn 204 is retracted away from the header module 12 and the next weld cycle is commenced.

In the ultrasonic welding process, the horn 204 is brought into contact with the surface 26 of the housing module 20 of header module 12 at the established static pressure. The applied static pressure is controlled by a depth and pressure setting module 230 that responds to the commanded static pressure value from the workstation 206 to operate the pressure fitting 210 to advance the horn surface against the surface of the header module 12. A feedback signal may be applied back to the depth and pressure setting module 230 to provide a feedback control function.

The pressure fitting 210 also controls the penetration depth of the horn 204 into the surface of the module housing 20 of header module 12 as the ultrasonic vibrations are converted into heat energy and melt the thermoplastic material. The control of the penetration depth is effected through feedback from a linear encoder 232 that is coupled to the assembly of the horn 204, transducer 212 and pressure fitting 210. The output signal of the linear encoder 232 is reset when the static pressure is first applied and then quantifies the advancement of the horn 204 from the initial position as ultrasonic energy is applied and commences to melt the thermoplastic material. When the output of the linear encoder 232 signifies that the penetration depth is achieved or will be achieved, the depth and pressure setting module 230 terminates the pressure and advancement of the horn 204.

During the application of ultrasonic energy, the amplitude of the ultrasonic vibrations is controlled by the amplitude control circuit 216 which responds to the commanded amplitude and a processed feedback signal from an amplitude detector 214. The amplitude setting signal is applied by the amplitude control circuit to the transducer 212 which vibrates the horn 204 at the prescribed ultrasonic frequency and amplitude. During the ultrasonic weld time, the amplitude is measured and converted to a feedback signal by the detector 214 that is applied to the bridge circuit 220 for comparison to the prescribed amplitude. A difference signal is generated by the bridge circuit 224 that is processed, filtered and amplified by a power circuit 224, filter circuit 226 and amplifier circuit 228 and applied to the amplitude control circuit 216 to modify the amplitude output signal applied to the transducer 212.

FIGS. 12–14 depict the manufacturing steps of attaching the pre-formed header module 12 to the enclosure attachment surface 38 of the hermetically sealed enclosure 14 in greater detail. The depicted attachment steps follow the assembly and welding of the hermetically sealed enclosure 12 to its lid, and the attachment of the tab base 56 to the lid to form the enclosure attachment surface 38 as described above. Moreover, the radiopaque ID plate 60 is already fitted into the plate channel 50, and the header electrode 70 is fitted into the position 70' of the electrode channel 28. The illustrated attachment steps can either follow or precede the attachment of the terminus of the feedthrough pin 40 to the interior surface of the header electrode 70.

FIG. 12 shows the initial steps of aligning and firmly seating the module attachment surface 48 against the enclosure attachment surface 38 such that the upstanding attachment tabs 52 and 54 are received in the respective tab channels 42 and 44, respectively. It will be understood that the feedthrough pin 40 is also extended through the feedthrough pin receiving channel 58 to bear against the interior surface of header electrode 70.

FIG. 13 shows the application of the ultrasonic horn 204 against a predetermined location of the module surface 26 in the manner depicted in FIG. 11. A static force of the pressure fitting 210 is applied through the ultrasonic horn 204 against the header module 12. The static force may itself slightly deform the module surface 26. Then, the ultrasonic transducer 212 is energized to vibrate the horn 204 at the selected ultrasonic frequency and amplitude for the selected time period to melt the thermoplastic material in the region of contact of the horn surface with the module surface 26. As the thermoplastic material melts, the applied force advances the surface of the horn 204 toward the region of the upstanding attachment tab 54 received in the tab channel 44. The generated heat causes the thermoplastic material of the module housing 20 to melt and flow ahead of the advancing horn surface. The tab hole 64 operates as a retention feature by accommodating the flow of the thermoplastic material through it during the application of ultrasonic energy in the region of the tab channel 44.

FIG. 14 illustrates the completion of the flow of the thermoplastic material into the tab channel 44 and through the tab hole 64 to encapsulate the attachment tab 54 that occurs as the surface of the ultrasonic horn 204 advances and penetrates the thermoplastic material. The penetration depth of advancement of the ultrasonic horn 204 is monitored by the linear encoder 232 of FIG. 11 and is terminated when the preset depth is reached. The time of application of ultrasonic energy is related to the time that it takes for the penetration depth to be achieved for the applicable dimensions of a given header module design. Upon termination of the ultrasonic energy, the thermoplastic housing material cools and solidifies to form a continuous rigid mass 20' that encapsulates the surface of the attachment tab 54 and the retention feature comprising the tab hole 64 in this illustration. The tab hole 64 accommodates a lateral (with respect to the direction the attachment tab 54 is extending) thermoplastic material flow through it, whereby the melted and solid thermoplastic material forms a continuous mass upon cooling and solidification.

The applied force and ultrasonic energy causes the face of the horn 204 to melt the area of contact with the module exterior surface 26 and create a slight depression 34 therein corresponding to the depth of penetration of the ultrasonic horn 204. The and the horn surface may be shaped and sized to minimize any cosmetic blemish that results.

After the ultrasonic energy is delivered, the horn 204 is preferably left in place for a short cooling period before it is withdrawn from the depression 34 and the assembled header module 12 and hermetically sealed enclosure 14 are moved. In this regard, the work piece holder 208 may automatically shift laterally over to align the horn to the location of the module surface 26 adjacent to the upstanding attachment tab 52 in the tab channel 42, and the ultrasonic welding process may be repeated.

It should be noted in the alternative that the horn 204 may be shaped to have two bearing surfaces that are spaced apart to match the spacing between the upstanding attachment tabs 52 and 54. In this variation, ultrasonic energy may be applied simultaneously to melt the thermoplastic material in the region around both of the upstanding attachment tabs and cause the thermoplastic material to flow through both of the tab bores 62 and 64 simultaneously.

It should also be noted that the horn surface of the ultrasonic horn 204 may be shaped to be placed at other surface locations of the module surface 26 than the illustrated locations. In general, it is necessary to shape the horn surface and locate the area of contact to avoid melting the thermoplastic material at areas of contact with other materials where vibration would occur. In this particular application of the first embodiment, such vibration could occur where the sides of the module electrode 70 contact the walls of the electrode channel 28 or the feedthrough terminal 40 contacts the terminal channel 58. In this instance, any resulting melting and flow of the thermoplastic material would likely be harmless as long as it is confined to the interior of these channels.

Figure 15:
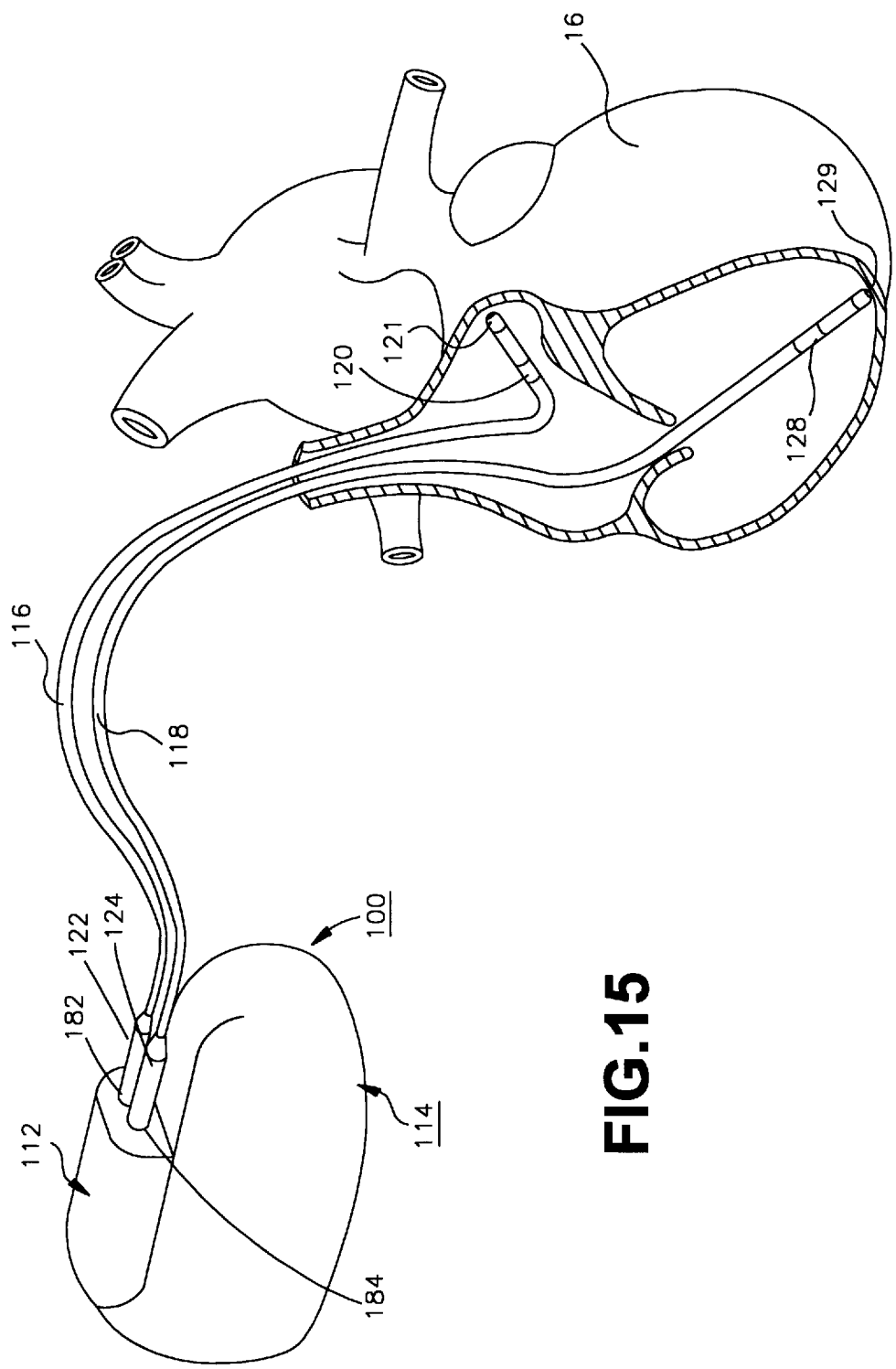
FIG. 15 is an isometric view of a cardiac pacemaker IPG and lead system in relation to a human heart in which the method of the present invention is practiced to attach a connector header module to the hermetically sealed enclosure thereof.

FIGS. 15–17 depict the application of the methods and apparatus of the present invention to the attachment of a connector header module 112 to the hermetically sealed enclosure 114 of a dual chamber pacemaker IPG 100. In FIG. 15, the completed dual chamber pacemaker IPG 100 is depicted in an implant relation to a patient's heart 10 wherein atrial and ventricular pacing leads 116 and 118 extend from the connector header module 112 to the right atrium and ventricle, respectively. Atrial electrodes 120 and 121 at the distal end of the atrial pacing lead 116 are located in the right atrium, and ventricular electrodes 128 and 129 at the distal end of the ventricular pacing lead 118 are located in the right ventricle. The connector header module 112 may take any of the forms described above for making the electrical and mechanical connections of the proximal connector end assemblies 122 and 124 of the atrial and ventricular pacing leads 116 and 118 to the electrical circuits within the hermetically sealed enclosure 114. The connector header module 112 therefore incorporates four connector blocks (not shown) within the module housing aligned with the elongated lead connector end receptacles 182 and 184 receiving the lead connector end assemblies 122 and 124, respectively. As in the first embodiment, the header module 112 is molded of a rigid thermoplastic, e.g., a medical grade polyurethane, housing having an exposed module surface and a number of receptacles and channels formed therein. The feedthroughs and feedthrough pins connected to the connector blocks and extending through the hermetically sealed enclosure can are also not shown in FIGS. 16 and 17 in order to simplify the illustration of the retention structure.

The retention feature and the method of attaching the connector header module 112 to the hermetically sealed enclosure 114 takes substantially the same form and steps as described above with respect to FIGS. 11–14. However, the components of the retention structure are duplicated because of the relatively increased size of the connector header module 112 and the mating module attachment surface 148 and enclosure attachment surface 138. In effect, each end of the elongated connector header module 112 is attached at two laterally displaced points to a respective corner of the enclosure attachment surface 138.

In this embodiment, two duplicate attachment tab assemblies 150, 150' that are spaced along the enclosure attachment surface 138 are employed to maximize the attachment peel and pull strength. The attachment tab assemblies 150, 150' comprise upstanding attachment tabs 152 and 154 and 152' and 154' that extend at right angles to opposite ends of attachment tab bases 156 and 156', respectively, and in parallel to one another. Tab bases 156, 156' are welded at predetermined locations to a flattened perimeter section of the can, and their exposed surfaces provide part of the enclosure attachment surface 138. The upstanding attachment tabs 152 and 154 and 152' and 154' are therefore opposed to one another across the width of the connector module 112. Each attachment tab 152, 154, 152', 154' also has tab holes 162, 164, 162', 164', respectively, formed therein to operate as retention features through which the melted thermoplastic material of the module housing flows and solidifies as described above.

In this case, the module attachment surface 148 is formed with base recesses 146 and 146' shown in FIG. 17 to accommodate the thickness of the tab bases 156 and 156', respectively. The tab channels 142, 144 and 142', 144' extend in parallel with one another and from the ends of the base recesses 146 and 146', respectively. In addition, a resilient cushioning gasket 190 is provided with openings 192 and 194 formed therein for accommodating the attachment tabs 152, 154 and 152', 154', respectively. Other openings would be provided for feedthrough terminals and other structure, if present.

In FIG. 16 the direction and location of the ultrasonic horn during application of ultrasonic energy is indicated by the horn depressions 132, 132'. It will be understood that a like pair of ultrasonic depressions would appear on the opposite planar major side of exterior surface 126 following attachment of the attachment tabs 154 and 154' as described above. Alternatively, ultrasonic energy may be applied over a wider area to effect the simultaneous melting and flow of the thermoplastic material of the module housing about each pair or all of the upstanding attachment tabs 152, 154 and 152', 154' and through the tab bores 162, 164 and 162', 164'.

In clinical use of the second embodiment, the proximal lead connector end assemblies 122 and 124 are inserted into the elongated lead connector receptacles 182 and 184, respectively, until the lead connector pin or ring is received in the bore of a connector block. The resilient O-ring seals of the lead connector end assemblies 122 and 124 received and compressed in the lead connector receptacles 182 and 184 and aligned connector block bores help to seal the electrical connections from body fluids. Then, each set screw is tightened by a hex wrench pressed through a penetrable silastic septum into engagement with the head of the set screw to rotate and tighten it to maintain the firm electrical and mechanical attachment. The present invention may be implemented into other configurations of connector headers 112 that employ other structures and methods for making electrical and mechanical connection between the lead connector end assembly(s) and the circuitry within the hermetically sealed enclosure 114.

The above-described assemblies and ultrasonic welding method employs a laterally extending retention feature comprising the upper edge of each tab hole extending laterally across each of the upstanding attachment tabs. This tab hole retention feature makes the relatively planar exterior surface of the upstanding attachment tabs more irregular. The ultrasonic energy is applied to the region of the irregular retention structure in the upstanding attachment tabs in the tab channels and the adjacent thermoplastic material of the pre-formed header module. The ultrasonic energy is of an amplitude and is applied for a duration sufficient to melt the adjacent thermoplastic material to flow around the laterally extending retention feature and provides the solid, laterally extending mass when the thermoplastic material solidifies after removal of the ultrasonic energy. The retention feature may take other forms that allow the laterally extending mass of solidified thermoplastic material to form and cooperate with the retention feature to form a strong retention structure that resists pulling or lateral bending of the header module housing off from the upstanding tabs.

FIGS. 18–19 and 20–21 are side cross-section views of first and second alternative laterally extending retention features of the upstanding attachment tabs that may be employed in lieu of the tab hole retention feature in each of the upstanding attachment tabs used in the retention structure. These alternative attachment retention features are illustrated in the context of a modification of the first embodiment header module and hermetically sealed enclosure, but are applicable to the second embodiment as well as other medical device embodiments. Moreover, the module and enclosure attachment surfaces are modified to resemble those of the second embodiment to minimize the space therebetween as generally described above.

In FIGS. 18 and 19, the retention feature is formed by a bent over hook 262 formed in the free end of the upstanding attachment tab 252. It bears against the side walls of the tab channel 242 in FIG. 18. FIG. 19 illustrates the flow of the mass 20' of the thermoplastic material of the module housing 20 into the tab channel 242 and under the hook 262 where it solidifies and provides strong retention of the header module 12 to the hermetically sealed enclosure 14. In this case, the module attachment surface 248 and the enclosure attachment surface 238 are relatively flat, and a base recess 246 is formed in the enclosure attachment surface 238 to accommodate the thickness of the attachment tab base 256.

In FIGS. 20 and 21, the retention feature is formed by an irregular, pleated shape of the upstanding attachment tab 352. The tab pleats bear against the side walls of the somewhat widened tab channel 342 in FIG. 20. FIG. 21 illustrates the flow of the mass 20' of the thermoplastic material of the module housing 20 into the tab channel 342 and around the tab pleats where it solidifies and provides strong retention of the header module 12 to the hermetically sealed enclosure 14. Again, in this case, the module attachment surface 348 and the enclosure attachment surface 338 are relatively flat, and a base recess 346 is formed in the enclosure attachment surface 338 to accommodate the thickness of the attachment tab base 356.

It will be understood that the retention feature may take other forms, e.g. a screw or corkscrew shape or any other irregular, fastener shape that allows the melted thermoplastic material to melt and flow somewhat in parallel with the plane of the enclosure and module attachment surfaces. The solidified thermoplastic material in the space between the module attachment surface and the retention feature thus extends laterally, and the lateral extension operates to resist pull and peel forces.

In the above-described preferred embodiments, the ultrasonic energy is applied through the module housing and the ultrasonic horn is not applied directly against the hermetically sealed enclosure of the attachment tabs extending therefrom. It may be possible to apply the ultrasonic horn directly to the metallic upstanding tab end in the region of the retention feature. Care must be taken to ensure that no harm to components within the hermetically sealed enclosure will result from the ultrasonic energy transmitted down the attachment tab.

The above described methods and apparatus for attaching a pre-formed header module to an implantable hermetically sealed enclosure may be applied to a wide variety of implantable medical devices having a variety of header module and hermetically sealed enclosure configurations. The principals of the present invention may be extended to permutations and combinations of these components of such implantable medical devices.

It should be noted that the term "upstanding" applied to the attachment tabs is intended to convey the meaning that the attachment tabs extend away from the enclosure attachment surface to a point where attachment may be made with a retention feature thereof. The attachment tabs need not extend perpendicularly away from the enclosure attachment surfaces or be bent at any particular angle with respect thereto as long as a retention force is achieved therebetween.

Moreover, the number and locations of the upstanding attachment tabs may vary from those depicted in the first and second embodiments. The attachment tabs may also be aligned at angles to one another that differ from the common plane alignment of the first embodiment attachment tabs 52 and 54 and the parallel plane alignments of the second embodiment attachment tabs 152, 152' and 154, 154'. For example, two or more upstanding attachment tabs may be aligned at 90° to one another.

The present invention achieves excellent peel and pull strengths with retention forces that are well above minimum specified test values established for assemblies that are attached using adhesive alone.

The preceding specific embodiments are illustrative of the practice of the invention. It is understood therefore that other expedients and equivalents of disclosed components or functions known to those of skill in the art or otherwise disclosed herein may be employed in practicing the invention without departing from the invention or the scope of the following claims.

In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures.

What is claimed is:

1. A method of attaching a hermetically sealed enclosure of an implantable medical device to a pre-formed thermoplastic material header module, comprising the steps of:

forming a retention structure extending away from an enclosure attachment surface of the hermetically sealed enclosure into proximity with a portion of the pre-formed header module when the enclosure attachment surface and a module attachment surface of the pre-formed header module are aligned in respect of one another, the retention structure comprising an upstanding attachment tab extending from a tab base to a tab free end and having an attachment feature disposed therein or thereon;

attaching the tab base to the hermetically sealed enclosure at a predetermined location, the upstanding attachment tab extending in a predetermined direction away from the enclosure surface, the retention feature being disposed at a location away from the enclosure attachment surface;

providing a tab channel in the header module, the tab channel being sized and oriented to receive the upstanding attachment tab therein when the enclosure attachment surface and the module attachment surface are aligned in respect of and brought into contact with one another;

aligning and firmly seating the module attachment surface against the enclosure attachment surface, the upstanding attachment tab being received in the tab channel of the header module, the attachment feature being disposed within the channel;

applying ultrasonic energy to a region of the pre-formed header module propinquant to the upstanding attachment tab and the tab channel, at least portions of the thermoplastic material of the header module in the region melting and flowing into intimate engagement with the upstanding tab and the attachment feature in response to the application of the ultrasonic energy thereto; and cooling the melted thermoplastic material until it solidifies around the upstanding attachment tab and the attachment feature.

2. The method of claim 1, further comprising the step of applying adhesive material between the enclosure attachment surface and the module attachment surface prior to the alignment and seating step.

3. The method of claim 1, wherein the retention structure forming step further comprises the step of forming a tab bore through the upstanding attachment tab to constitute the attachment feature and the ultrasonic energy application step further comprises applying ultrasonic energy to the region having an amplitude and for a duration of time sufficient to melt at least portions of the thermoplastic material in the region, the thermoplastic material flowing through the tab bore and extending therethrough, the thermoplastic material solidifying after the ultrasonic energy is no longer applied to the region.

4. The method of claim 1, where the retention structure forming step further comprises the step of forming a tab hook in the free end of the upstanding attachment tabs, the tab hook forming the attachment feature and the ultrasonic energy application step further comprises applying ultrasonic energy to the region having an amplitude and for a duration of time sufficient to melt at least portions of thermoplastic material in the region, the thermoplastic material flowing around the tab hook, the thermoplastic material solidifying after the ultrasonic energy is no longer applied to the region.

5. The method of claim 1, wherein:

the retention structure forming step further comprises the step of forming tab pleats in the upstanding attachment tab, the tab pleats forming the attachment feature; and the ultrasonic energy application step further comprises applying ultrasonic energy to the region having an amplitude and for a duration of time sufficient to melt at least portions of the thermoplastic material in the region, the thermoplastic material flowing around the tab pleats when the thermoplastic material solidifies after removal of the ultrasonic energy.

6. The method of claim 1, wherein the retention structure forming step further comprises the step of forming irregularly laterally extending means for retention extending laterally in respect of the upstanding attachment tab and the ultrasonic energy application step further comprises applying ultrasonic energy to the region having an amplitude and for a duration of time sufficient to melt at least portions of the thermoplastic material in the region, the thermoplastic material flowing around the laterally extending retention means, the thermoplastic material solidifying after the ultrasonic energy is no longer applied to the region.

7. The method of claim 1, further comprising the steps of fabricating a pre-formed spacer of a compressible body compatible material shaped to conform to the enclosure attachment surface and the header module attachment surface and fitting the pre-formed spacer between the enclosure attachment surface and the header module attachment surface to provide a seal therebetween.

8. The method of claim 1, wherein the tab forming step further comprises forming a pair of upstanding attachment tabs extending in parallel in respect of one another from respective ends of the tab base, each tab having a retention feature disposed therein;

the tab base attaching step further comprises attaching the tab base to a predetermined location of the enclosure attachment surface, each upstanding attachment tab extending in a predetermined direction away from the enclosure surface;

the tab channel providing step further comprises providing a pair of tab channels spaced apart from one another, disposed in the header module, and sized to receive the upstanding attachment tabs when the enclosure attachment surface and the module attachment surface engage and are aligned respecting one another; and the aligning and firmly seating step further comprises aligning the module attachment surface with the enclosure attachment surface, the upstanding attachment tabs being received in the tab channels.

9. The method of claim 8, further comprising the steps of fabricating a pre-formed spacer comprising a compressible body compatible material, the spacer being shaped to be disposed between and to conform to the enclosure attachment surface and the module attachment surface and fitting the pre-formed spacer between the enclosure attachment surface and the header module attachment surface to provide a seal therebetween.

10. The method of claim 8, wherein the retention structure forming step further comprises the step of disposing a tab bore through at least portions of each of the upstanding attachment tabs to form the respective retention features.

11. The method of claim 8, wherein the retention structure forming step further comprises the step of forming a tab hook in the free end of each of the upstanding attachment tabs to form the respective attachment features.

12. The method of claim 8, wherein the retention structure forming step further comprises the step of forming tab pleats in each of the upstanding attachment tabs to form the respective attachment features.

13. The method of claim 8, wherein the retention structure forming step further comprises the step of forming irregularly laterally extending means for retention in each of the upstanding attachment tabs.

14. The method of claim 8, further comprising the step of: applying adhesive material between the enclosure attachment surface and the module attachment surface prior to the aligning and firmly seating step.

* * * * *